United States Patent
Vouillamoz et al.

(10) Patent No.: US 10,671,022 B2
(45) Date of Patent: Jun. 2, 2020

(54) SYSTEMS AND METHODS FOR INDICATING A QUANTITY

(71) Applicant: Preciflex SA, Neuchâtel (CH)

(72) Inventors: Lucien Vouillamoz, Feusisberg (CH); Yves Ruffieux, St-Aubin (CH)

(73) Assignee: Preciflex SA, Nêuchatel (CH)

(*) Notice: Subject to any disclaimer, the term of this patent is extended or adjusted under 35 U.S.C. 154(b) by 18 days.

(21) Appl. No.: 15/301,437

(22) PCT Filed: Apr. 7, 2015

(86) PCT No.: PCT/IB2015/000446
§ 371 (c)(1),
(2) Date: Oct. 3, 2016

(87) PCT Pub. No.: WO2015/150909
PCT Pub. Date: Oct. 8, 2015

(65) Prior Publication Data
US 2017/0235278 A1    Aug. 17, 2017

Related U.S. Application Data

(60) Provisional application No. 61/974,448, filed on Apr. 3, 2014, provisional application No. 62/033,686, filed (Continued)

(30) Foreign Application Priority Data

Apr. 7, 2015   (WO) .................. PCT/IB2015/000448

(51) Int. Cl.
*G04G 9/00*   (2006.01)
*G04B 19/00*   (2006.01)
(Continued)

(52) U.S. Cl.
CPC .............. *G04B 19/00* (2013.01); *G04B 1/26* (2013.01); *G04B 39/02* (2013.01); *G04G 9/00* (2013.01)

(58) Field of Classification Search
CPC .......... G04B 1/26; G04B 19/00; G04B 39/02; G04G 9/00
(Continued)

(56) References Cited

U.S. PATENT DOCUMENTS 3,242,733 A * 3/1966 Johnson .................... G01K 3/04
                                                            374/102
3,414,415 A * 12/1968 Broad, Jr. ................ G01K 3/04
                                                            116/219
(Continued)

FOREIGN PATENT DOCUMENTS

FR       1552838 A     1/1969

OTHER PUBLICATIONS

Chapter 2 of Electrohydrodynamic and Magnetohydrodynamic Micropumps—2007.*
(Continued)

*Primary Examiner* — Sean Kayes
(74) *Attorney, Agent, or Firm* — Da Vinci Partners LLC; John Moetteli (57) ABSTRACT

An indication device is provided which has an electrically conductive fluid driven by an MHD pump. The fluid has an indicator surface driven adjacent indices of an indicator so as to indicate a quantity. A position of the indicator surface is sensed and controlled to ensure accurate indication of the quantity. Optionally, the quantity indicated is time.

20 Claims, 12 Drawing Sheets

Related U.S. Application Data on Aug. 6, 2014, provisional application No. 61/985,492, filed on Apr. 29, 2014, provisional application No. 62/143,904, filed on Apr. 7, 2015.

(51) Int. Cl.
*G04B 39/02* (2006.01)
*G04B 1/26* (2006.01)

(58) Field of Classification Search
USPC .......................................................... 368/327
See application file for complete search history.

(56) References Cited

U.S. PATENT DOCUMENTS

| | | | | |
|---|---|---|---|---|
| 3,783,598 | A | 1/1974 | Parr | |
| 4,228,649 | A * | 10/1980 | Weiss ........................ | G04F 1/08 |
| | | | | 368/93 |
| 4,629,330 | A * | 12/1986 | Nichols .................... | G01K 3/04 |
| | | | | 116/216 |
| 6,973,894 | B1 * | 12/2005 | Adamy ................ | G01N 31/229 |
| | | | | 116/200 |
| 2009/0219789 | A1 | 9/2009 | Meadows | |
| 2012/0263022 | A1 * | 10/2012 | Grize ..................... | G04B 19/00 |
| | | | | 368/226 |

OTHER PUBLICATIONS

International Search Report of International Patent Application No. PCT/IB2015/000446, dated Oct. 8, 2015.

* cited by examiner

SYSTEMS AND METHODS FOR INDICATING A QUANTITY

CROSS REFERENCE TO RELATED APPLICATION(S)

This application is a PCT application claiming priority to U.S. application No. 61/974,448, filed 3 Apr. 2014, entitled SYSTEMS AND METHODS FOR ABSORBTION/EXPANSION OF A LIQUID IN A TRANSPARENT CAVITY, to U.S. application Ser. No. 13/422,438, filed 16 Mar. 2012, entitled WRISTWATCH, to U.S. application Ser. No. 14/083,538, filed 19 Nov. 2013, entitled FLUID INDICATOR, to U.S. application No. 62/033,686, filed on 6 Aug. 2014, entitled TIME KEEPING DEVICES INCLUDING INDICATIONS BY MAGNETIC PARTICLES IN SUSPENSION IN LIQUID FILLED CHAMBERS, to U.S. application 61/985,492, filed 29 Apr. 2014, entitled STEERING AND VELOCITY CONTROL OF A MENISCUS SYSTEM AND METHOD, AND TIME PIECE SYSTEM INCORPORATING SAME, to U.S. application 62/143,904, filed 7 Apr. 2015, entitled WATCH WITH LIQUID INDICATION, and to PCT/IB2015/000446, filed 7 Apr. 2015, entitled SYSTEMS AND METHODS FOR ABSORBTION/EXPANSION/CONTRACTION/MOVEMENT OF A LIQUID IN A TRANSPARENT CAVITY the contents of the entirety of which are explicitly incorporated herein by reference and relied upon to define features for which protection may be sought hereby as it is believed that the entirety thereof contributes to solving the technical problem underlying the invention, some features that may be mentioned hereunder being of particular importance.

COPYRIGHT & LEGAL NOTICE

A portion of the disclosure of this patent document contains material which is subject to copyright protection. The Applicant has no objection to the facsimile reproduction by anyone of the patent document or the patent disclosure as it appears in the Patent and Trademark Office patent file or records, but otherwise reserves all copyright rights whatsoever. Further, no references to third party patents or articles made herein are to be construed as an admission that the present invention is not entitled to antedate such material by virtue of prior invention.

BACKGROUND OF THE INVENTION

This invention relates to systems and methods for timepieces that include movement/absorption/expansion/contraction of a liquid in a transparent cavity, particularly in wristwatches.

Luxury watches exist that indicate time using a meniscus of a liquid which is driven by a purely mechanical system. Such watches are complicated and, consequently, very expensive. A need therefore exists for a low cost, electronic watch that accurately indicates time using the meniscus of a liquid.

SUMMARY OF THE INVENTION

The invention provides a system for a device. The system for a device includes a channel finable with one or more liquids. The individual liquids are preferable immiscible with each other. Each individual liquid can be transparent or colored, have the same refractivity as the substrate, can optionally contain solid particles, can be electrical conductive or electrical non-conductive. In a variant, the indication is done with a moving gas bubble, such as a radioactive tritium gas. The channel is formed as a closed loop or in a variant formed with ends ending in a reservoir. An electrically conductive liquid can be moved with the channel by the means of one or more magnetohydrodynamic pumps (MHD pumps). If a further variant, a second liquid is electrical non-conductive or electrically conductive, this liquid is pushed or pulled by the electrically conductive liquid driven by the MHD pump(s).

In a variant, the position of the electrically non-conductive or electrical conductive liquid, in a variant embodied as a gas bubble, within the channel is sensed along the channel by its deviating dielectricity between the two or more liquids. The sensing of the capacitance or the sensing of the change of the capacitance is preferably made by a number of capacitors spread along the channel.

In another variant, the channel is used in a timepiece. The permanent magnets and/or electrodes required in MHD pumps, in order to be non-visible to a user, are incorporated into design/decoration elements or hidden by design/decoration elements. In another variant, the permanent magnets and/or electrodes are visible to the user.

In another variant, the capacitors used to sense the dielectricity or the change of the dielectricity is accomplished with sputtering, preferable as ITO (Indium-tin oxine) or FTO (Fluorin-doped tin oxine).

In another variant, the channel is formed as a micro capillary.

In another variant, the channel is formed by two or more glass wafers, preferably connected to each other by a suitable bonding process.

In another variant, the channel is formed by two or more polymer wafers, preferably connected to each other by a suitable bonding process.

In another variant, a membrane is embedded between wafers.

In another variant, the channel system has one or more open access holes to allow an initial filling of the system with liquid(s), implicating an automated filling of the system during the production process. Through one access hole, a liquid is inserted, while another access hole provides access to ambient pressure. After initial filling, the access hole(s) are closed in a fluid and/or gas tight manner. Optional, the access hole(s) can be opened and closed again, e.g. for maintenance reasons.

In another variant, as well for a closed loop system, as for a variant with ends ending in a reservoir, is equipped with a system to compensate thermal expansion/contraction of the liquid(s). This is accomplished by a thin and therefore flexible wafer, or a separate gas chamber, or a flexible soft material part, or a membrane. The flexible soft material part can be placed in the channel or in a separate chamber, which is in fluid communication with the channel. The compensation system is non-visible to a user, and in another variant visible to the user. The non-visible system is disposed underneath the visible system.

Those skilled in the art will appreciate that elements in the Figures are illustrated for simplicity and clarity and have not necessarily been drawn to scale. For example, dimensions may be exaggerated relative to other elements to help improve understanding of the invention and its embodiments. Furthermore, when the terms 'first', 'second', and the like are used herein, their use is intended for distinguishing between similar elements and not necessarily for describing a sequential or chronological order. Moreover, relative terms like 'front', 'back', 'top' and 'bottom', and the like in the Description and/or in the claims are not necessarily used for describing exclusive relative position. Those skilled in the art will therefore understand that such terms may be interchangeable with other terms, and that the embodiments described herein are capable of operating in other orientations than those explicitly illustrated or otherwise described.

DETAILED DESCRIPTION OF THE PREFERRED EMBODIMENT

The following description is not intended to limit the scope of the invention in any way as it is exemplary in nature, serving to describe the best mode of the invention known to the inventors as of the filing date hereof. Consequently, changes may be made in the arrangement and/or function of any of the elements described in the exemplary embodiments disclosed herein without departing from the spirit and scope of the invention.

Figure 1:
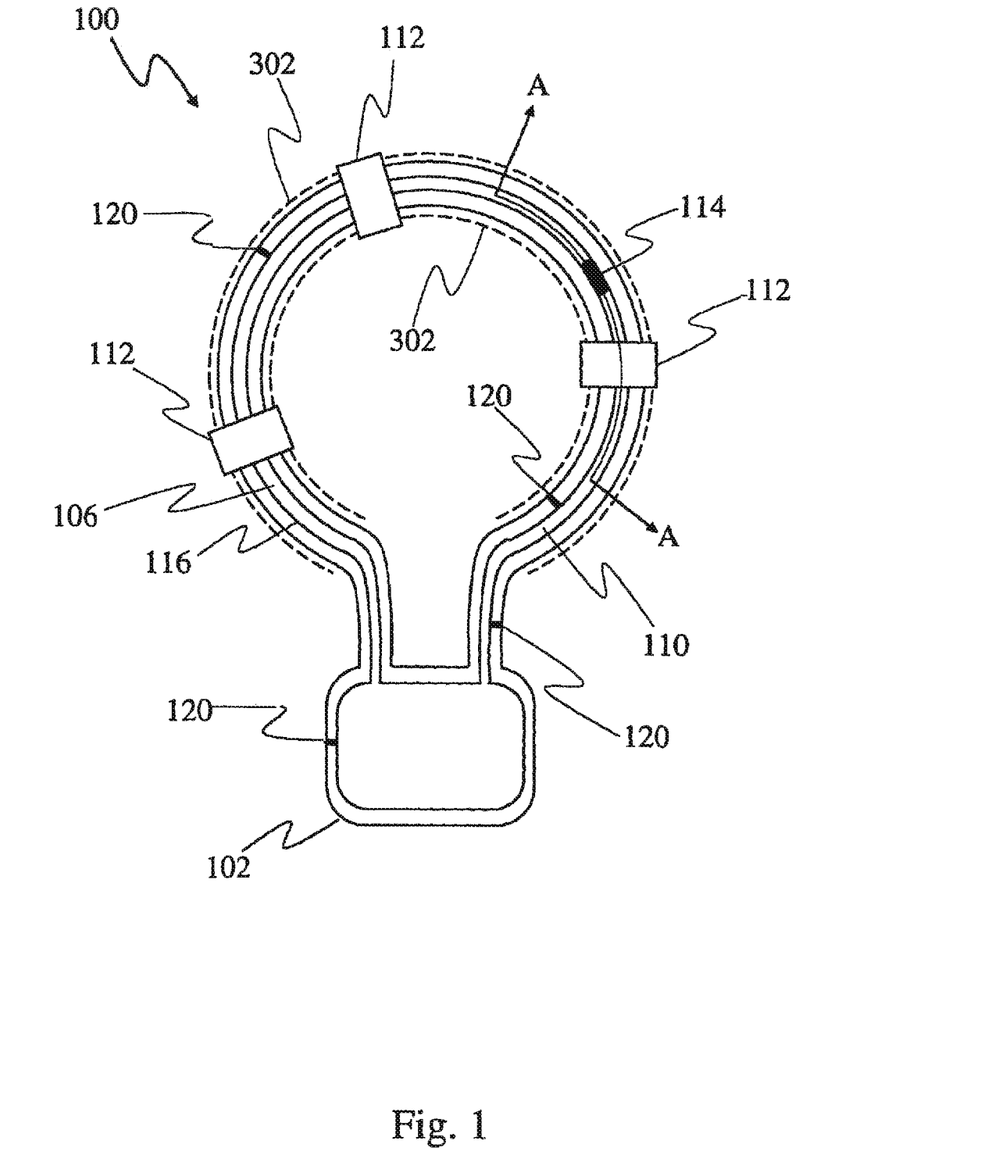
FIG. 1 is a schematic top view of the invention.

FIG. 1 is a top view of a system 100 including a capillary channel 116, at its both ends having a reservoir 102 attached. It is appreciated that the capillary channel 116 can take on a variety of geometric cross-sectional two dimensional or three dimensional cross-sectional and overall shapes or configurations, e.g. a cylindrical tube, a square, a rectangle, a circle, an oval, an oval shape, a triangular shape, a pentagonal shape, a hexagonal shape, an octagonal shape, a cubic shape, a spherical shape, an egg shape, a cone shape, a dome shape, a rectangular prism shape, and a pyramidal shape, by way of further example. In this variant the capillary channel 116 is filled with a first essentially electrically conductive, optionally colored liquid 106, implicating for example a Sodium chloride solution and a second electrically conductive or electrically non-conductive, optionally colored liquid 114, implicating for example a silicone oil or a liquid sapphire (as used herein, any liquid having the same refractivity as the substrate), in a variant accomplished using a gas bubble. Of course, the system can contain more or less liquids and another combination of different liquids. Further, this variant is equipped with one or more magnetohydrodynamic pumps (MHD pumps) 112. The channel 116 has optionally one or more open access holes 120 to allow an initial filling of the system with liquid(s), implicating an automated filling of the system during the production process. The system is further equipped with capacitors 302. The system does compensate thermal expansions and compressions of a liquid 106 located in the channel 202, as proposed in FIGS. 7 to 11.

Figure 2:
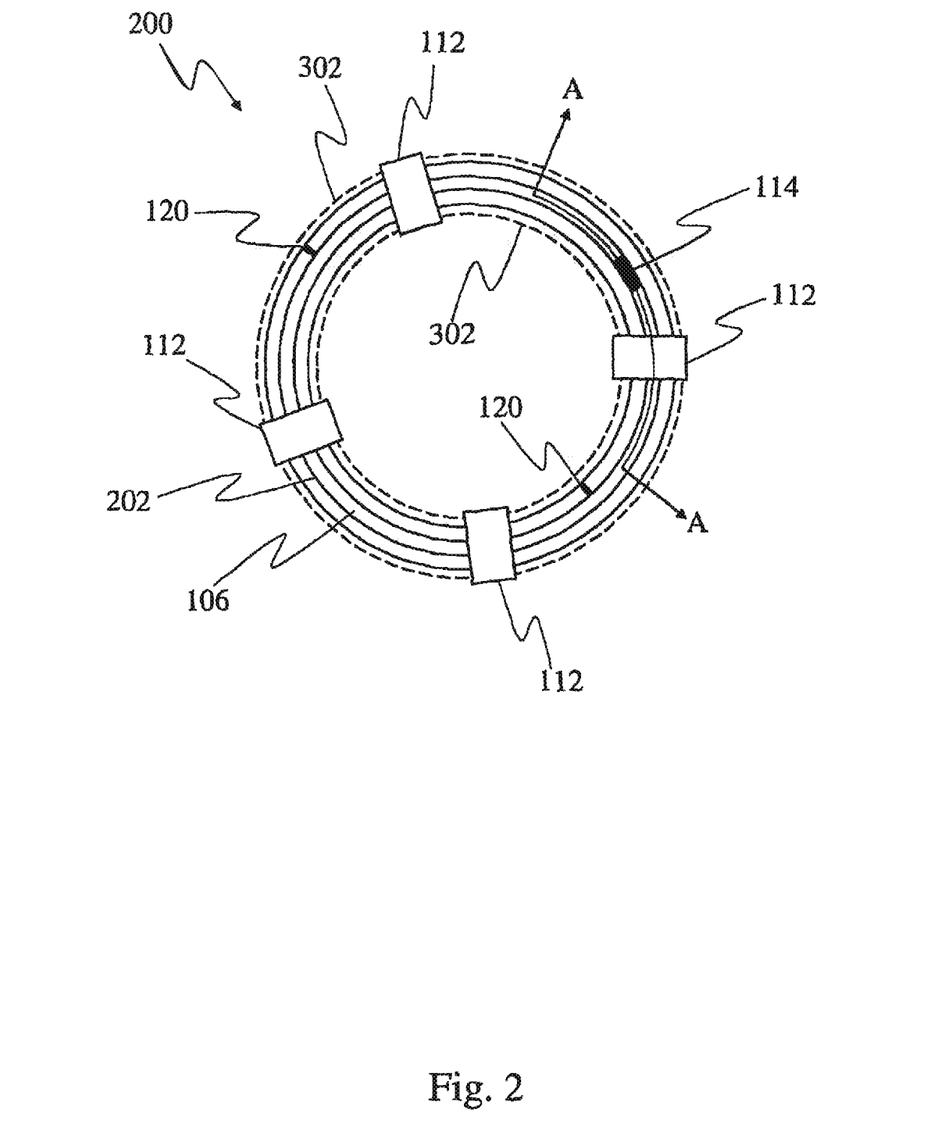
FIG. 2 is a schematic top view of the invention in another variant.

FIG. 2 is a top view of a system 200 including a capillary channel 202 formed as a closed loop. It is appreciated that the capillary channel 202 can take on a variety of geometric cross-sectional two dimensional or three dimensional cross-sectional and overall shapes or configurations as mentioned above. In this variant the capillary channel 202 is filled with a first essentially electrically conductive, optionally colored liquid 106, implicating for example a Sodium chloride solution and a second electrically conductive or electrically non-conductive, optionally colored liquid 114, implicating for example a silicone oil or liquid sapphire, in a variant accomplished using a gas bubble. Of course, the system can contain more or less liquids and another combination of different liquids. Further, this variant is equipped with one or more magnetohydrodynamic pumps (MHD pumps) 112. The channel 202 has optionally one or more open access holes 120 to allow an initial filling of the system with liquid(s), implicating an automated filling of the system during the production process. The system is further equipped with capacitors 302. The system does compensate thermal expansions and compressions of a liquid 106 located in the channel 202, as proposed in FIGS. 7 to 11.

Figure 3:
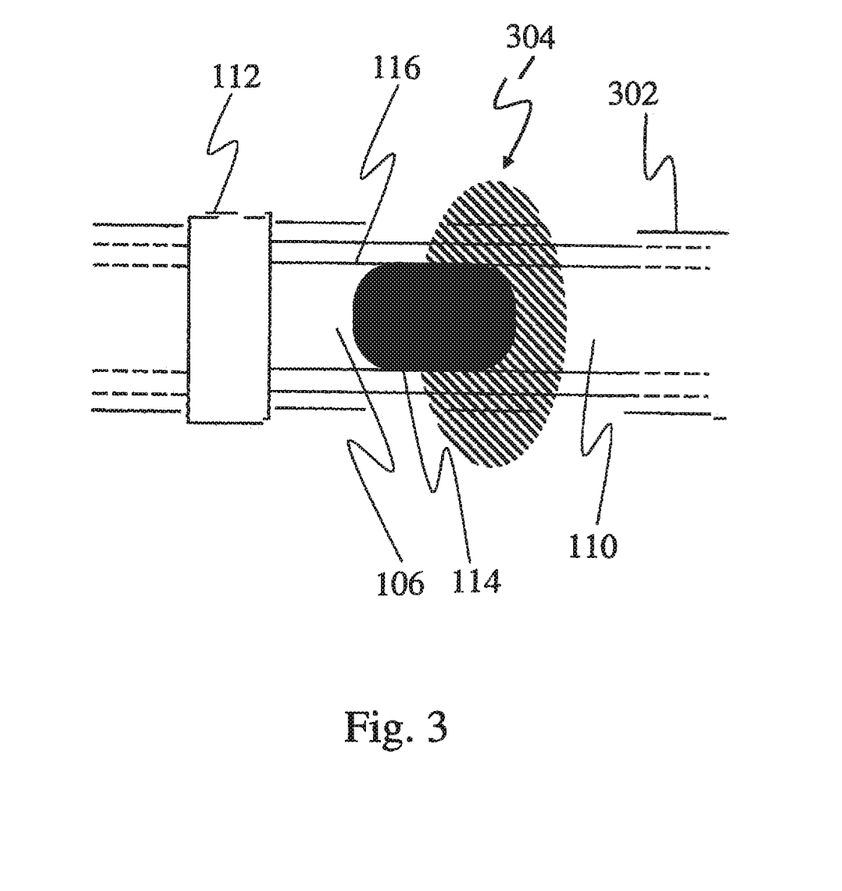
FIG. 3 is a detail view of an indicator liquid arrangement of the invention.

FIG. 3 is a sectional view A-A of FIG. 1 including a capillary channel 116. In this variant the capillary channel 116 is filled with a first essentially electrically conductive, optionally colored liquid 106, implicating for example a Sodium chloride solution and a second electrically conductive or electrically non-conductive, optionally colored liquid 114, implicating for example a silicone oil or liquid sapphire, and in a variant accomplished using a gas bubble. Of course, the system can contain more or less liquids and another combination of different liquids. Further, this variant is equipped with one or more magnetohydrodynamic pumps (MHD pumps) 112 to drive an electrically conductive or a non-conductive, optionally colored liquid 114, implicating for example a silicone oil or liquid sapphire, in a variant accomplished using a gas bubble, surrounded by an optionally colored, transparent conductive liquid 110. The system is further equipped with capacitors 302 used to sense the dielectricity or the change of the dielectricity essentially at areas 304 near the capacitor or the pair of capacitor or the triple of capacitors. The capacitors are made by sputtering, preferable as ITO (Indium-tin oxine) or FTO (Fluorin-doped tin oxine). Several capacitors are placed along the channel 116. The dielectricity and/or the change of dielectricity can be sensed by dedicating one, a pair or a triple of capacitors to an area 304.

Figure 4:
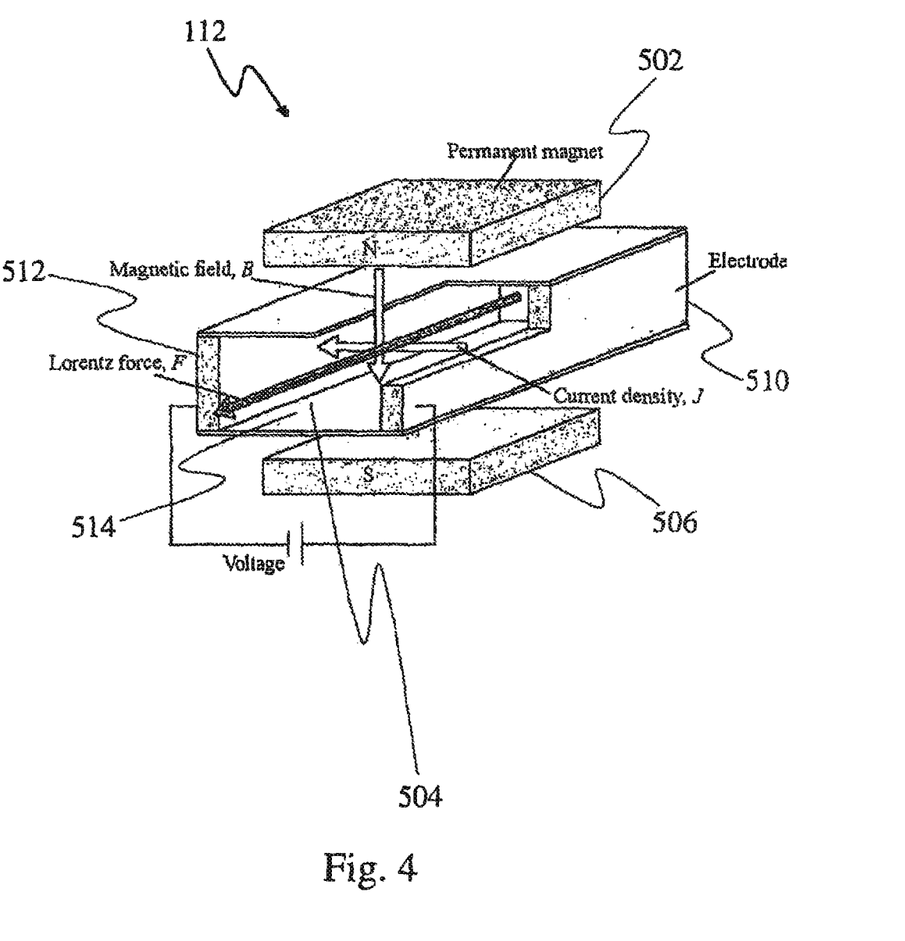
FIG. 4 is a schematic perspective view of an MHD motor used in the invention.

FIG. 4 is a perspective view of a magnetohydrodynamic pumps (MHD pumps) 112. The MHD pump 112 includes a permanent magnet with its polarization North 502 directed towards a channel 504, a permanent magnet with its polarization South 506 directed towards a channel 504 and essentially opposite to permanent magnet with its polarization North 502. The channel contains liquids 514, implicating for example a silicone oil, liquid sapphire or a Sodium chloride solution, in a variant accomplished using a gas bubble. The system is further equipped with a pair of electrodes 510, 512, reframing the channel 504 and essentially 90° to the permanent magnets 502, 506. To the electrodes 510, 512 a direct current (DC), positive or negative polarized, can be applied. The swap of polarization will reverse the flow of the liquids 514. The permanent magnets 502, 506 may either be in contact with the liquids 514 or not be in contact with the liquids 514 and/or gas. The electrodes 510, 512 are in contact with the liquids 514 and/or gas.

Considering the circular capillary sub-systems 100 or 200, and its various dimensions, a time of 60 seconds is used to completely fill the circular capillary sub-system 100 or 200. An exemplary specification for a robust, efficient, fit for purpose MHD pump 112 is as follows:

| | |
|---|---|
| 1. Capillary sub-system 100 or 200 cross-sectional area: | $A = 0.5$ mm$^2$ |
| 2. MHD flow mean velocity: | $V_{MHD} = $ 1.895 mm/s |
| 3. MHD flow rate: | $Q_{MHD} = $ 57.165 µL/min |

Of course, the stronger the MHD pump 112 is the more fluid is moved into cavity 116 or 202 at a faster rate. Slower rates of filling are accomplished by weaker MHD pumps 112 depending on their overall specifications and pumping strength.

Now looking at other MHD pump variants in the comparison provided below, and summarized in Table 1 below, it is appreciated that the example highlighted in red approximates the required specifications. Other MHD pumps can be used, depending upon the requirements of fluid movement, either continuous or intermittent, or those that require faster or slower fluid movement in the cavity 116 or 202. It is appreciated that an MHD pump 112, and circular capillary sub-system 100 or 200 featuring cavity 116 or 202 is provided in another variant. Other variants of dimensions (area, volume, geometric shape) of components of sub-system 100 or 200 are also provided in combination with other MHD pumps that have other engineered properties and modes of operation, some being fit for purpose and some not, but preferably, the specifications of MHD pump 112 underlined in Table 1 are preferable for optimal fluid movement in cavity 116 or 202.

The following list of references with respect to MHD pumps are incorporated into this patent application by reference in their entirety, showing the variety of MHD pumps in the market:
1. Design, Microfabrication, and Characterization of MHD Pumps and their Applications in NMR Environments, Thesis by Alexandra Homsy, 2006, the content of which is incorporated herein by reference thereto.
2. Bislug Flow in Circular and Noncircular Channels and the Role of Interface Stretching on Energy Dissipation, Thesis by Joseph E. Hernandez, August 2008, the content of which is incorporated herein by reference thereto.

In yet a further aspect, the invention also provides for a grouping of sub-systems that include a circular (or other geometric configuration) capillary sub-system(s) with one or more MHD pumps 112. The groups include one or more MHD pumps 112 and tube/cavity combinations or groups of inter-related sub-systems. The one or more than one MHD pump 112 manages displacement of one or more fluids within individual circular capillary sub-systems or by way of manifold into more than one capillary sub-systems, in series or in parallel, alone or in combination with other MHD pumps providing for multiple indicator functionality within a single device, e.g. a wristwatch.

Figure 5:
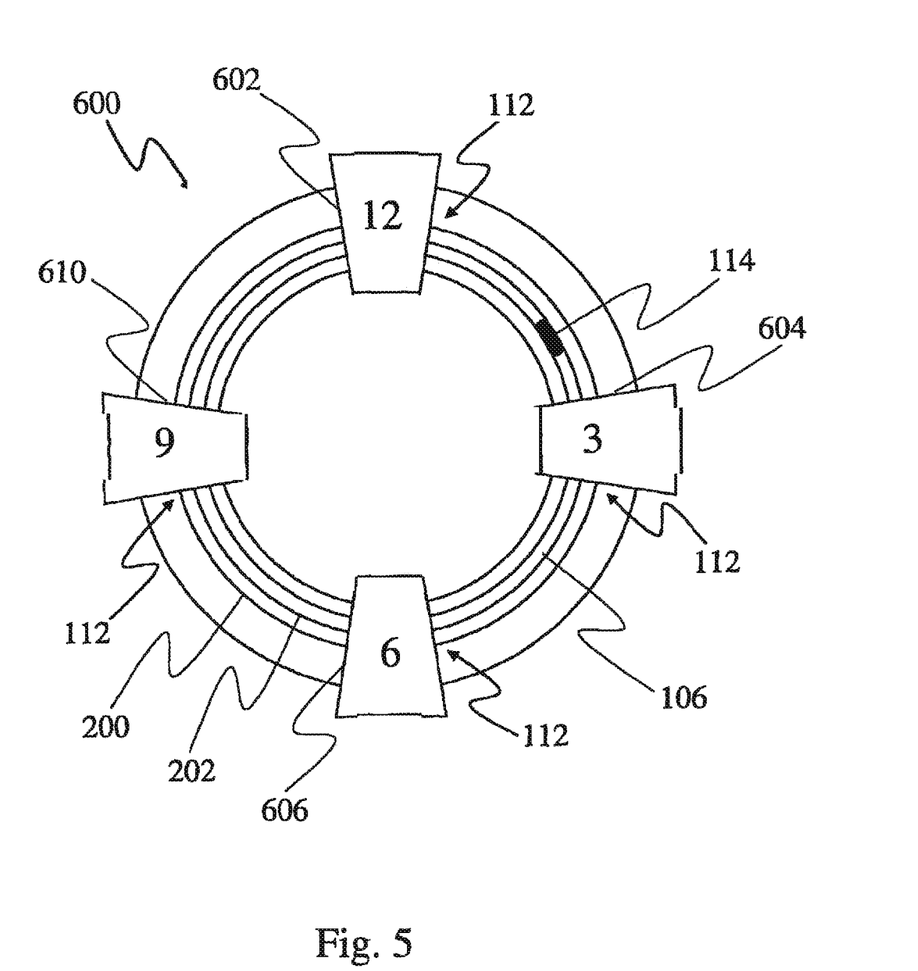
FIG. 5 is a schematic top view of the invention in another variant.

FIG. 5 is a perspective view of a timepiece 600 equipped with system 200. The system 200 includes a capillary channel 202 formed as a closed loop. In this variant the capillary channel 202 is filled with a first essentially electrically conductive liquid 106, implicating for example a Sodium chloride solution and a second electrically conductive or electrically non-conductive, optionally colored liquid 114, implicating for example silicone oil or liquid sapphire, in a variant accomplished using a gas bubble. Of course, the system can contain more or less liquids and another combination of different liquids. Further, this variant is equipped with four magnetohydrodynamic pumps (MHD pumps) 112. The magnetohydrodynamic pumps (MHD pumps) are incorporated into design/decoration elements or hidden by design/decoration elements 602, 604, 606, 610, in order to be non-visible to a user.

Figure 6:
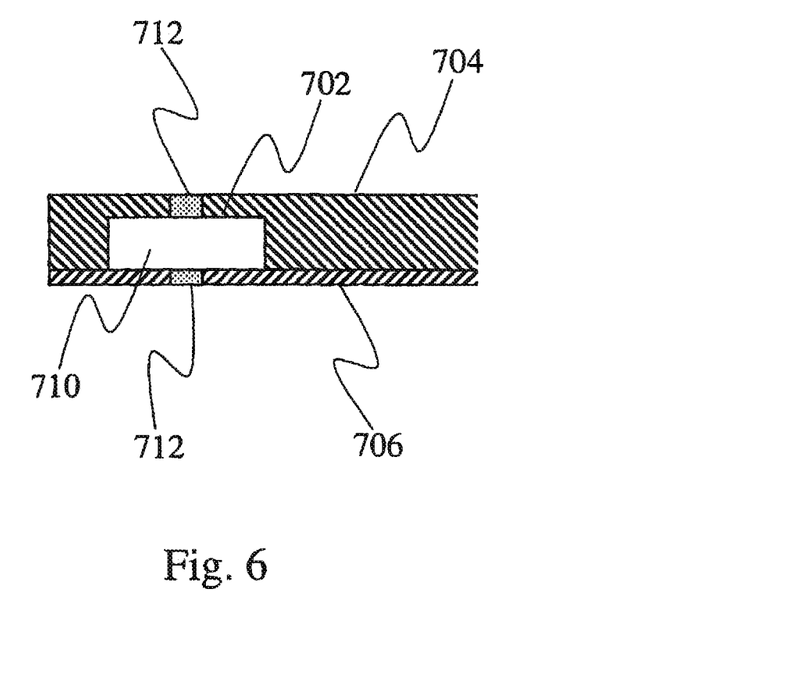
FIG. 6 is a cross sectional detail view of the liquid reservoir of the invention.

FIG. 6 is a cross sectional view of variant of system 100 or system 200. The channel 702 is formed by two wafers 704, 706, implicating wafers made out of glass and/or polymer. The wafers 704, 706 are fixed to each other preferably by a suitable bonding process. The channel 702 contains one or more liquids and/or gas 710, implicating for

TABLE 8.1

Performance comparison of previously published MHD pumps with our MHD pump presented in Ch 4 and 6. All values for voltage (U), current (I), channel cross-sectIonal area (A), total length of electrodes along the pumping channel (l). MHD flow mean velocity in the pumping channel ($v_{MHD}$) and MHD flow rate ($Q_{MHD}$) were experimental data, and were taken from references [1-6]. Most of the values for the electrode cross-sectional area ($A_f$) and current density (J) across the pumping channel had to be calculated. The body force ($\Delta P_{MHD}$) generated by the pumps was calculated thanks to relation 2.14.

| | U (V) | I (mA) | A (mm$^2$) | $A_f$ (mm$^2$) | l (num) | J (A·m$^{-2}$) | B (T) | $\Delta P_{MHD}$ (Pa) | $v_{MHD}$ (mm·s$^{-1}$) | $Q_{MHD}$ (µL·min$^{-1}$) |
|---|---|---|---|---|---|---|---|---|---|---|
| Jang et al. [1] | 30 DC | 1.8 | 0.4 | 30 | 30 | 60 | 0.44 | 1 | 2.6* | 63* |
| Leventis et al. [2] | >1.3 DC | 35 | 18 | 225 | 75 | 155 | 1.35 | 16 | 0.4 | 450·10$^3$ |
| Bau et al. [3] | 4 DC | 15 | 1.9 | 292 | 172 | 51 | 0.4 | 3.5 | 0.4 | 45 |
| Lemoff et al. [4] | 6.6 AC | 140 | 0.2 | 1.5 | 4 | 92105 | 0.013 | 5 | 1.5 | 18 |
| West et al. [5] | 5 AC | 90 | 0.2 | 5 | 28 | 17684 | 0.011 | 5.5 | 0.24 | 3 |
| Bijkel et el. [6] | 4 AC | 40 | 6·10$^{-3}$ | 2 | 63 | 21100 | 0.1 | 133 | 0.04 | 14·10$^{-3}$ |
| Chapter 4 | 16 DC | 4.8 | 8.8·10$^{-3}$ | 1.2 | 16 | 4000 | 0.42 | 27 | 0.5 | 0.3 |
| Chapter 6 | 19 DC | 2 | 8.8·10$^{-3}$ | 1.2 | 16 | 1600 | 7.05 | 180 | 2.8 | 1.5 |

*Both values were taken from experimental measurements. If calculated with relations 2.16 and 2.15, the predicted velocity and flow rate would be 0.16 mm·s$^{-1}$ and 4 µL·min$^{-1}$ respectively.

example a silicone oil, liquid sapphire or a Sodium chloride solution. Wafer 706 is particularly thin in the region of the channel 702 and is therefore enough flexible in that region to compensate thermal expansions and compressions of a liquid 710 located in the channel 702. The channel 702 has optionally one or more open access holes 712 to allow an initial filling of the system with liquid(s) 710, implicating an automated filling of the system during the production process.

Figure 7:
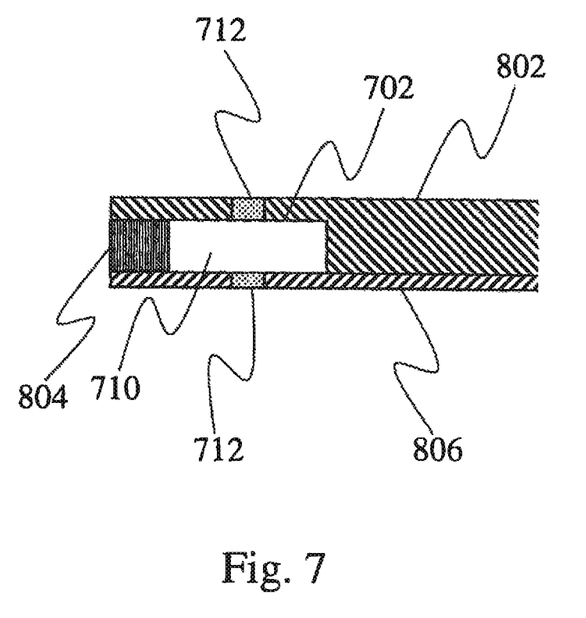
FIG. 7 is a cross sectional detail view of a variant of the liquid reservoir of the invention.

FIG. 7 is a cross sectional view of variant of system 100 or system 200. The channel 702 is formed by three or more wafers 802, 804, 806, implicating wafers made out of glass and/or polymer. The wafers 802, 804, 806 are fixed to each other preferably by a suitable bonding process. The channel 702 contains one or more liquids and/or gas 710, implicating for example a silicone oil, liquid sapphire or a Sodium chloride solution. Wafer 806 is particularly thin in the region of the channel 702 and is therefore enough flexible in that region to compensate thermal expansions and compressions of a liquid 710 located in the channel 702. The channel 702 has optionally one or more open access holes 712 to allow an initial filling of the system with liquid(s) 710, implicating an automated filling of the system during the production process.

Figure 8:
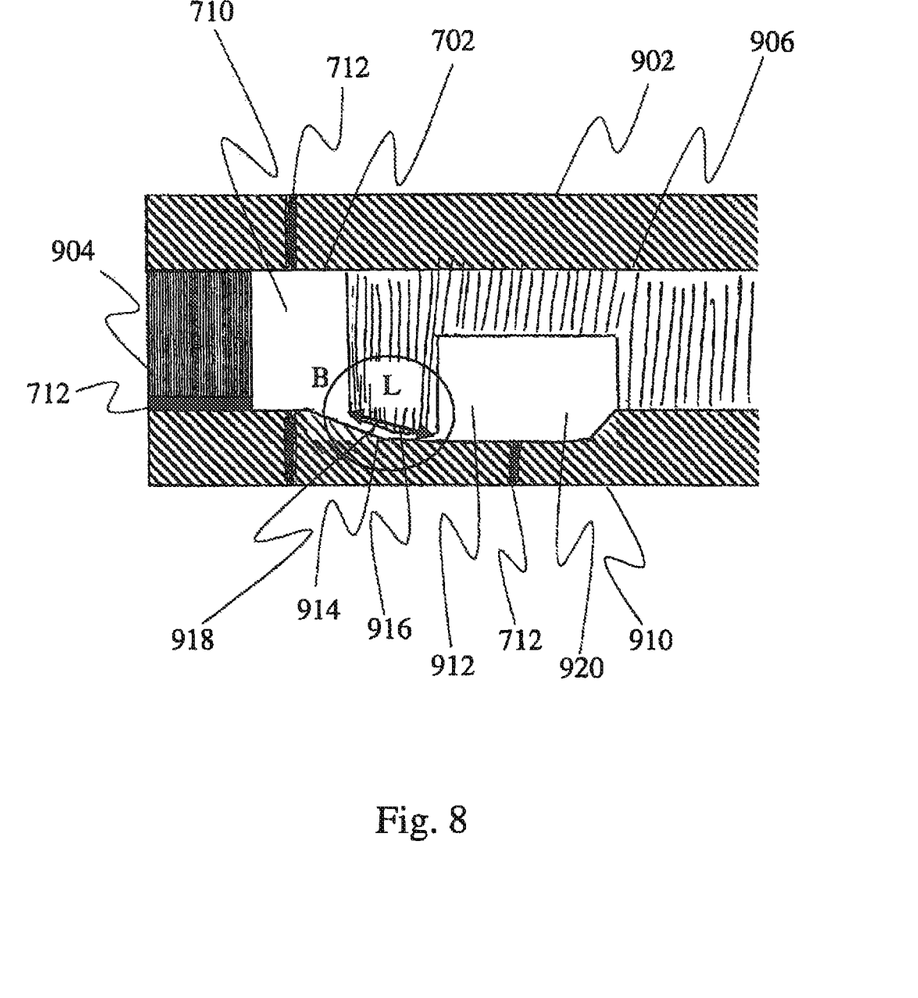
FIG. 8 is a cross sectional detail view of another variant of the liquid reservoir of the invention.

FIG. 8 is a cross sectional view of variant of system 100 or system 200. The channel 702 is formed by four wafers 902, 904, 906, 910, implicating wafers made out of glass and/or polymer. The system can also be formed by less or more wafers. The wafers 902, 904, 906, 910 are fixed to each other preferably by a suitable bonding process. The channel 702 contains one or more liquids 710, implicating for example a silicone oil, liquid sapphire or a Sodium chloride solution. Wafers 906, 910 form a gas chamber 912 containing essentially gas 920. Gas chamber 912 and channel 702 are connected to each other through a thin transit passage 914. The thin transit passage has a certain length 916, typically 0.5-2 mm. The intersection 918 between gas 920 and liquid 710 is essentially within the length 916. The compressibility of gas 920 in combination with this system allows to compensate thermal expansions and compressions of a liquid 710 located in the channel 702. The channel 702 and/or the gas chamber 912 has optionally one or more open access holes 712 to allow an initial filling of the system with liquid(s) 710 and/or gas 920, implicating an automated filling of the system during the production process.

Figure 9:
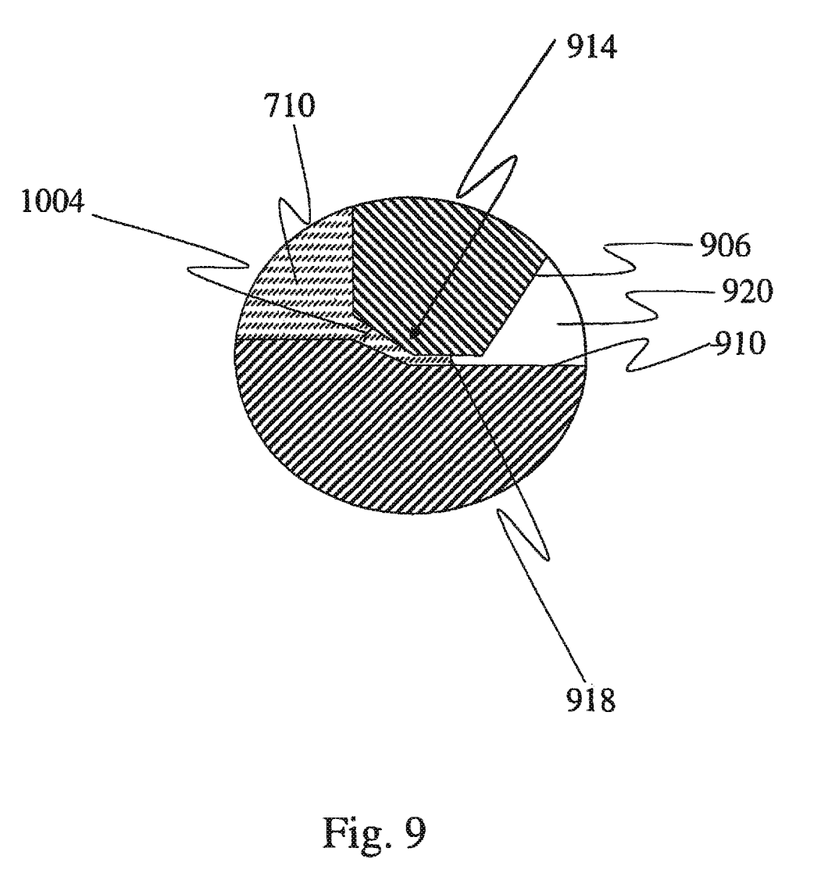
FIG. 9 is a cross sectional view of a detail view of an element of FIG. 8.

FIG. 9 is the detail view B of FIG. 8. The thin transit passage 914 is shown in detail. To optimize the trapping of a liquids 710, the angle 1004 between wafers 906, 910 at the entrance of the thin transit passage can be positive, zero or negative. The forming of the thin transit passage 914 can further be freely chosen in order to optimize a proper separation of gas 920 and liquid 710. To prevent mixing or migration of gas 920 from gas chamber 912 to the channel 702, the dimensions and shape of the thin transit passage 914 has to be adapted according to the viscosities of the liquids 710.

Figure 10:
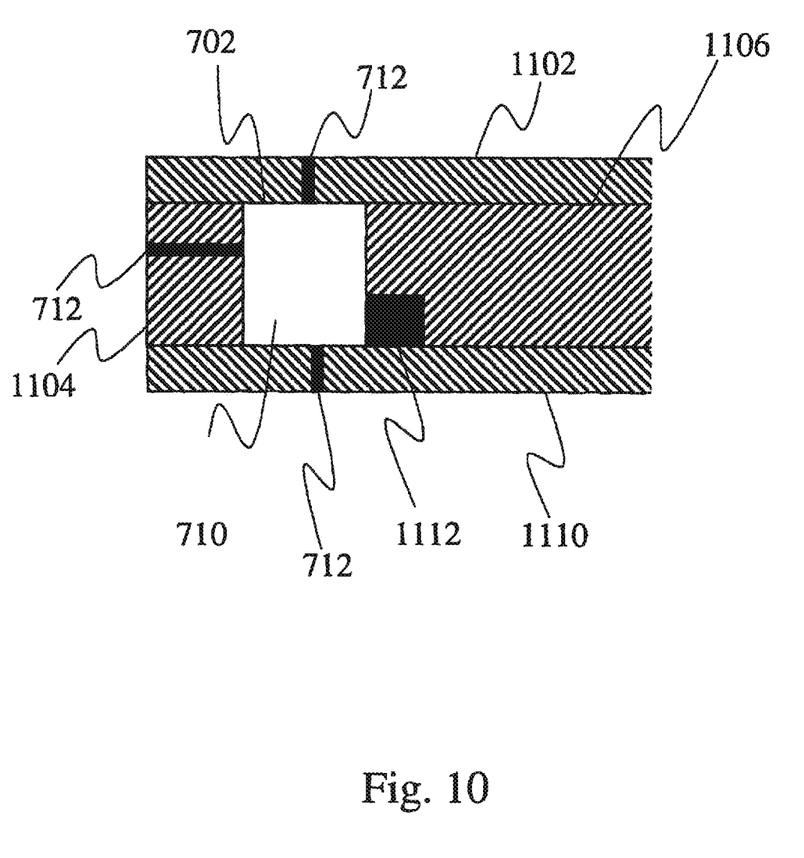
FIG. 10 is a cross sectional detail view of still another variant of the liquid reservoir of the invention.

FIG. 10 is a cross sectional view of variant of system 100 or system 200. The channel 702 is formed by four wafers 1102, 1104, 1106, 1110, implicating wafers made out of glass and/or polymer. The system can also be formed by less or more wafers. The wafers 1102, 1104, 1106, 1110 are fixed to each other preferably by a suitable bonding process. The channel 702 contains one or more liquids 710, implicating for example a silicone oil, liquid sapphire or a Sodium chloride solution, in a variant accomplished using a gas bubble. A soft material 1112 is located at a specific place to be in contact with the liquid and/or gas 710. The soft material 1112 has the property to compensate thermal expansions and compressions of a liquid 710 located in the channel 702. The channel 702 has optionally one or more open access holes 712 to allow an initial filling of the system with liquid(s) and or gas 710, implicating an automated filling of the system during the production process.

Figure 11:
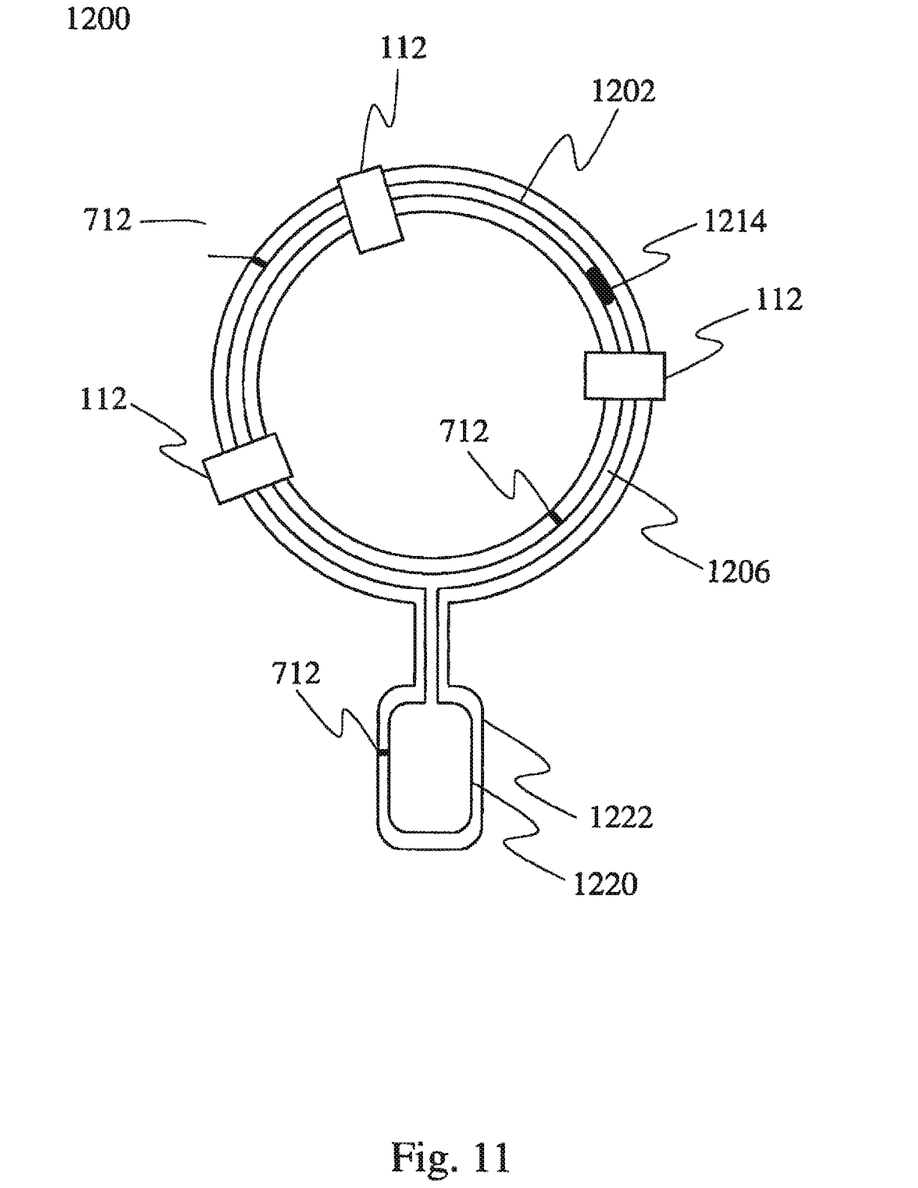
FIG. 11 is a schematic top view of the invention in another variant.

FIG. 11 is a top view of a system 1200 including a capillary channel 1202 formed as a closed loop. It is appreciated that the capillary channel 1202 can take on a variety of geometric cross-sectional two dimensional or three dimensional cross-sectional and overall shapes or configurations. In this variant the capillary channel 1202 is filled with a first essentially electrically conductive, optionally colored liquid 1206, implicating for example a Sodium chloride solution and a second electrically conductive or electrically non-conductive, optionally colored liquid 1214, implicating for example a silicone oil or liquid sapphire, in a variant accomplished using a gas bubble. Of course, the system can contain more or less liquids and another combination of different liquids. Further, this variant is equipped with one or more magnetohydrodynamic pumps (MHD pumps) 112. A reservoir 1220 is located at a specific place in fluid communication with the channel 1202. The housing 1222 of the reservoir 1220 has the ability to compensate thermal expansions and compressions of a liquid 1206 located in the channel 1202. Such compensation, however, may also be obtained such as described in FIG. 3 of PCT/IB2015/000446, filed 7 Apr. 2015, entitled SYSTEMS AND METHODS FOR ABSORBTION/EXPANSION/CONTRACTION/MOVEMENT OF A LIQUID IN A TRANSPARENT CAVITY. The channel 1202 and/or the housing 1222 of the reservoir 1220 has optionally one or more open access holes 712 to allow an initial filling of the system with liquid(s) or gas 1206, 1214, implicating an automated filling of the system during the production process.

Figure 12:
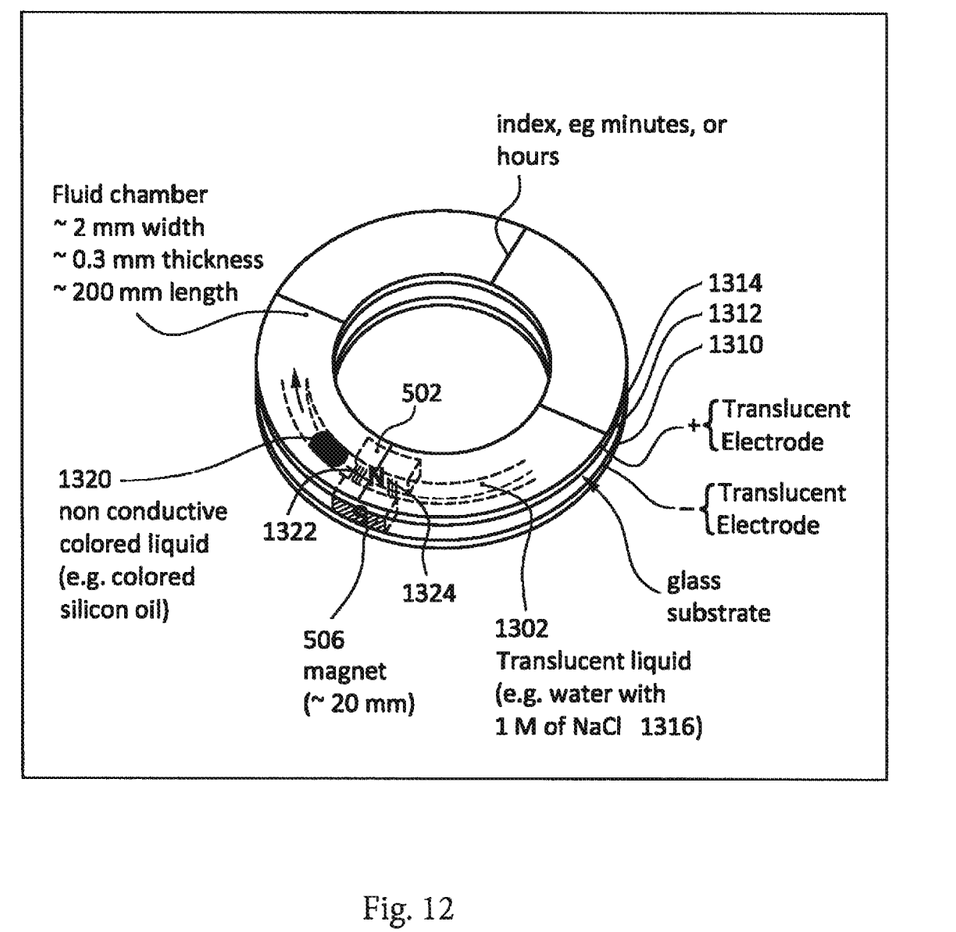
FIG. 12 is a schematic perspective view of the invention in still another variant.

FIG. 12 is a variant of a system as e.g. described in FIG. 2, FIG. 5 or FIG. 11, including a closed loop 1302. The channel 1306 is formed by fixing two or more wafers 1310, 1312, 1314 together, implicating wafers made out of glass and/or polymer. The channel 1306 may be filled with fluid, gas, solid particles or a combination thereof. In this variant, the channel is filled with two different types of fluids 1316, 1320, implicating for example a silicone oil, liquid sapphire or a Sodium chloride solution. At least one of the filled liquids is essentially electrically conductive. An MHD pump 112 is integrated having its permanent magnets 502, 506 placed along the inner diameter and along the outer diameter between two wafers 1310, 1314. Further, wafer 1310 and wafer 1314 are electrically conductive and function as electrodes. The electrical conductivity on wafers 1310, 1314 are preferable achieved by sputtering, preferable as ITO (Indium-tin oxine) or FTO (Fluorin-doped tin oxine). The essentially electrically conductive liquid 1316 will be driven forward or backwards by a Lorenz force, created by the magnetic field 1322 generated by the permanent magnets 502, 506 in combination with the electrical field 1324 generated between the two wafers 1310, 1314 connected to a direct current (DC) voltage source. The swap of polarization will reverse the flow of the liquids 1316, 1320. Of course, this variant contains mechanism to compensate thermal expansion and/or contractions of the fluid, as described before. And of course, this variant contains capacitors to measure the dielectricity and/or the change of dielectricity as described in FIG. 3.

The instant provisional patent application incorporates by reference in its entirety, as if fully set forth herein, U.S.

patent application Ser. No. 61/787,727, filed on 15 Mar. 2013, and International patent application no. PCT/IB2014/000373, filed on 17 Mar. 2014, both entitled "TEMPERATURE DRIVEN WINDING SYSTEM".

As used herein, the terms "comprises", "comprising", or variations thereof, are intended to refer to a non-exclusive listing of elements, such that any apparatus, process, method, article, or composition of the invention that comprises a list of elements, that does not include only those elements recited, but may also include other elements described in the instant specification. Unless otherwise explicitly stated, the use of the term "consisting" or "consisting of" or "consisting essentially of" is not intended to limit the scope of the invention to the enumerated elements named thereafter, unless otherwise indicated. Other combinations and/or modifications of the above-described elements, materials or structures used in the practice of the present invention may be varied or adapted by the skilled artisan to other designs without departing from the general principles of the invention. The patents and articles mentioned above are hereby incorporated by reference herein, unless otherwise noted, to the extent that the same are not inconsistent with this disclosure.

Other characteristics and modes of execution of the invention are described in the appended claims. Further, the invention should be considered as comprising all possible combinations of every feature described in the instant specification, appended claims, and/or drawing figures which may be considered new, inventive and industrially applicable.

Copyright may be owned by the Applicant(s) or their assignee and, with respect to express Licensees to third parties of the rights defined in one or more claims herein, no implied license is granted herein to use the invention as defined in the remaining claims. Further, vis-à-vis the public or third parties, no express or implied license is granted to prepare derivative works based on this patent specification, inclusive of the appendix hereto.

Additional features and functionality of the invention are described in the claims appended hereto. Such claims are hereby incorporated in their entirety by reference thereto in this specification and should be considered as part of the application as filed.

Multiple variations and modifications are possible in the embodiments of the invention described here. Although certain illustrative embodiments of the invention have been shown and described here, a wide range of changes, modifications, and substitutions is contemplated in the foregoing disclosure. While the above description contains many specific details, these should not be construed as limitations on the scope of the invention, but rather exemplify one or another preferred embodiment thereof. In some instances, some features of the present invention may be employed without a corresponding use of the other features. Accordingly, it is appropriate that the foregoing description be construed broadly and understood as being illustrative only, the spirit and scope of the invention being limited only by the claims which ultimately issue in this application.

What is claimed is:

1. A wristwatch comprising a wrist band and at least one electrically conductive liquid driven by at least one pump for conductive liquids, wherein at least one segment of at least one liquid is used as an indicator in a capillary channel, said segment visible to an observer so as to indicate time to the observer, which segment the pump drives along adjacent indices of the indicator of time, wherein further the at least one liquid is enclosed in a rigid chamber of a closed loop that has at least one exposed, at least partially transparent surface allowing the observer to observe the position of the at least one segment of the liquid, the device further comprising a mechanism accommodating thermal expansion and/or contraction of the liquids, the mechanism being a gas-filled chamber portion of the rigid chamber disposed out of the field of view of the observer so as to be substantially invisible to the observer, wherein a meniscus of the segment of the at least one liquid is sensed and controlled to position the meniscus at a desired position to ensure accurate indication of time, and wherein capacitance or conductance is used to detect the position of the segment of the at least one liquid, so as to enable control thereof.

2. The device of claim 1, wherein the mechanism accommodating thermal expansion and/or contraction is a gas-filled indicator bubble in the at least one liquid.

3. The device of claim 1, wherein the mechanism accommodating thermal expansion or contraction is selected from a group of mechanisms consisting of a thin and flexible wafer enclosing the chamber in an airtight and watertight manner and disposed out of the field of view of the observer, a separate gas-filled chamber disposed out of the field of view of the observer, and a soft flexible material disposed in a portion of the chamber which is out of the field of view of the observer.

4. The device of claim 1, wherein the mechanism accommodating thermal expansion and/or contraction is a gas-filled chamber portion of the rigid chamber connected to the liquid-filled portion of the rigid chamber by a passageway portion of the rigid chamber.

5. The device of claim 1, wherein the pump is at least one MHD pump.

6. The device of claim 5, wherein the direction of motion of the liquid is changed by changing the polarity of the at least one MHD pump.

7. The device of claim 1, wherein at least one liquid is a colored liquid.

8. The device of claim 1 in which the at least one liquid has the same refractive index as the rigid chamber.

9. The device of claim 1, wherein the at least one liquid has a suspended particulate visible to the observer.

10. The device of claim 1, wherein the liquid is contained in an elongated chamber.

11. The device of claim 10, wherein the elongated chamber is linear in form in portions thereof.

12. The device of claim 10, wherein the elongated chamber is nonlinear in form, preferably circular.

13. The device of claim 1, wherein the chamber is formed by two or more wafers, preferably connected to each other by bonding.

14. The device of claim 1, wherein the wafers are glass wafers.

15. The device of claim 14, wherein the chamber is formed by injection molding of the polymer.

16. The device of claim 1, wherein the chamber is formed by a polymer.

17. The device of claim 1, wherein the pump is at least two MHD pumps spaced apart along the elongated chamber so as to ensure that at any operational position of the liquid, the liquid can be pumped.

18. An indication device comprising at least one electrically conductive liquid driven by at least one magnetic pump for conductive liquids, wherein at least one segment of at least one liquid is used as an indicator, said segment visible to an observer so as to indicate a time quantity to the observer, which segment the pump drives along adjacent indices of the indicator of time, wherein further the at least one liquid is enclosed in a rigid chamber of a closed loop that has at least one exposed, at least partially transparent surface allowing the observer to observe the position of the at least one segment of the liquid, the device further comprising a mechanism accommodating thermal expansion and/or contraction of the liquids, the mechanism being a gas-filled chamber portion of the rigid chamber disposed out of the field of view of the observer so as to be substantially invisible to the observer.

19. An indication device comprising at least one electrically conductive liquid driven by at least one magnetic pump for conductive liquids, wherein at least one segment of at least one liquid is used as an indicator, said segment visible to an observer so as to indicate a time quantity to the observer, which segment the pump drives along adjacent indices of the indicator of time, wherein further the at least one liquid is enclosed in a rigid chamber of a closed loop that has at least one exposed, at least partially transparent surface allowing the observer to observe the position of the at least one segment of the liquid, the device further comprising a mechanism accommodating thermal expansion and/or contraction of the liquids, the mechanism being a gas-filled chamber portion of the rigid chamber disposed out of the field of view of the observer so as to be substantially invisible to the observer, wherein further, the chamber is formed by two or more wafers, preferably connected to each other by bonding.

20. An indication device comprising at least one electrically conductive liquid driven by at least one magnetic pump for conductive liquids, wherein at least one segment of at least one liquid is used as an indicator, said segment visible to an observer so as to indicate a time quantity to the observer, which segment the pump drives along adjacent indices of the indicator of time, wherein further the at least one liquid is enclosed in a rigid chamber of a closed loop that has at least one exposed, at least partially transparent surface allowing the observer to observe the position of the at least one segment of the liquid, the device further comprising a mechanism accommodating thermal expansion and/or contraction of the liquids, the mechanism being a gas-filled chamber portion of the rigid chamber disposed out of the field of view of the observer so as to be substantially invisible to the observer, wherein further the wafers are glass wafers.

* * * * *